US010573002B2

(12) United States Patent
Lakshmi et al.

(10) Patent No.: US 10,573,002 B2
(45) Date of Patent: Feb. 25, 2020

(54) IMAGE PROCESSING METHOD AND APPARATUS FOR NORMALISATION AND ARTEFACT CORRECTION

(71) Applicant: KONINKLIJKE PHILIPS N.V., Eindhoven (NL)

(72) Inventors: Priya Lakshmi, Belfast (GB); Jim Diamond, Belfast (GB); Peter Hamilton, Belfast (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/761,597

(22) PCT Filed: Sep. 23, 2016

(86) PCT No.: PCT/GB2016/052969
§ 371 (c)(1),
(2) Date: Mar. 20, 2018

(87) PCT Pub. No.: WO2017/051187
PCT Pub. Date: Mar. 30, 2017

(65) Prior Publication Data
US 2018/0357765 A1 Dec. 13, 2018

(30) Foreign Application Priority Data

Sep. 23, 2015 (GB) .................................. 1516866.9

(51) Int. Cl.
*G06K 9/00* (2006.01)
*G06T 7/00* (2017.01)
(Continued)

(52) U.S. Cl.
CPC ............. *G06T 7/0014* (2013.01); *G01N 1/30* (2013.01); *G06T 5/001* (2013.01); *G06T 5/009* (2013.01);
(Continued)

(58) Field of Classification Search
CPC ................ G01N 1/30; G01N 2001/302; G06T 2207/10056; G06T 2207/20021;
(Continued)

(56) References Cited

U.S. PATENT DOCUMENTS 5,991,028 A * 11/1999 Cabib .................. C12Q 1/6816
356/456
5,995,645 A * 11/1999 Soenksen ........... G01B 11/0675
356/328

(Continued)

FOREIGN PATENT DOCUMENTS

WO 2013022688 A1 2/2013

OTHER PUBLICATIONS

Vicory, Jared et al "Appearance Normalization of Histology SLides" Computerized Medical Imaging and Graphics, vol. 43, Jul. 1, 2015, pp. 89-98.

(Continued)

*Primary Examiner* — Tom Y Lu
(74) *Attorney, Agent, or Firm* — Sherry Austin

(57) ABSTRACT

A computer implemented image processing for normalizing images is disclosed. The method comprises calculating, for each chunk of an image, a combination of the two largest contributions to the variations of color of the chunk that approximates a representation of three additive color component data elements of the each image chunk, thereby to provide a plurality of approximated image chunks. The approximated image chunks are used to determine (i) a first item of approximated image chunk data, vMin, that corresponds to a first one of the two largest contributions, and (ii) a second item of the approximated image chunk data, vMax, that corresponds to a second one of the two largest contributions, wherein the first item of approximated image chunk data and the second item of approximated image chunk data (Continued)

together provide a mapping transformation and for each image pixel, image pixel data is obtained comprising three additive color component data elements of the each image pixel, and transformed using the mapping transformation to calculate normalized image pixel data for the each image pixel.

21 Claims, 5 Drawing Sheets

(51) Int. Cl.
*G06T 5/00* (2006.01)
*G06T 7/42* (2017.01)
*G01N 1/30* (2006.01)

(52) U.S. Cl.
CPC .......... *G06T 7/42* (2017.01); *G01N 2001/302* (2013.01); *G06T 2207/10056* (2013.01); *G06T 2207/20021* (2013.01); *G06T 2207/30024* (2013.01)

(58) Field of Classification Search
CPC ........... G06T 2207/30024; G06T 5/001; G06T 5/009; G06T 7/0014; G06T 7/42
See application file for complete search history.

(56) References Cited

U.S. PATENT DOCUMENTS

| | | | |
|---|---|---|---|
| 6,718,053 B1* | 4/2004 | Ellis | G01N 15/1475 345/604 |
| 7,321,791 B2 | 1/2008 | Levenson | |
| 2005/0065440 A1 | 3/2005 | Levenson | |
| 2010/0329535 A1 | 12/2010 | Macenko | |
| 2012/0112098 A1* | 5/2012 | Hoyt | B82Y 30/00 250/459.1 |
| 2017/0161545 A1* | 6/2017 | Champlin | G06K 9/0014 |

OTHER PUBLICATIONS

Kuru, K. et al "A Bilinear Interpolation Based Approach for Optimizing Hematoxylin and Eosin Stained Microscopical Images", Pattern Recognition in Bioinformatics, 6th IAPR Interional Conf. Nov. 2011, ISBN 978-3-642-24854-2, pp. 168-178.

* cited by examiner

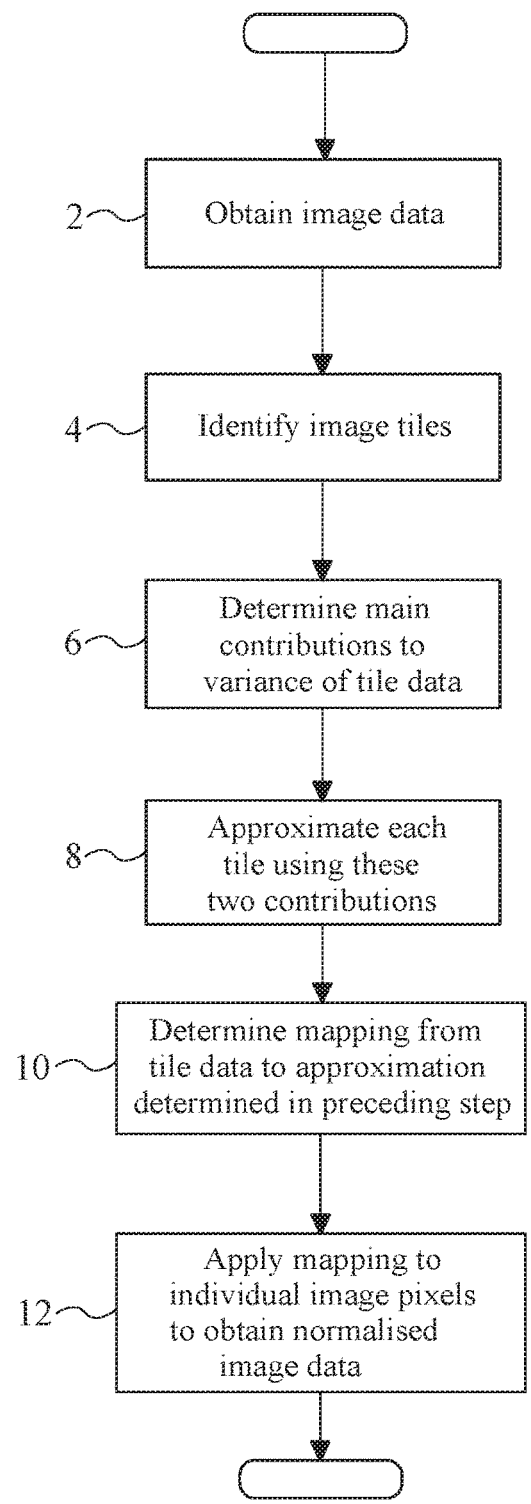
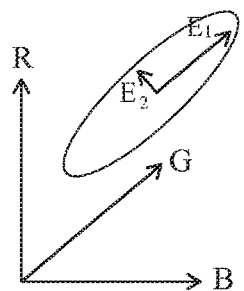
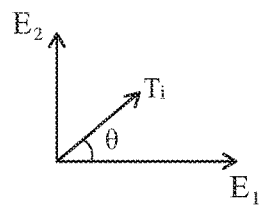
$$\theta_i = \arctan\left(\frac{|E_1|}{|E_2|} \frac{E_2 \cdot T_i}{E_1 \cdot T_i}\right)$$
*Fig. 1B*
*Fig. 1A*

IMAGE PROCESSING METHOD AND APPARATUS FOR NORMALISATION AND ARTEFACT CORRECTION

CROSS-REFERENCE TO PRIOR APPLICATIONS

This application is the U.S. National Phase application under 35 U.S.C. § 371 of International Application No. PCT/GB2016/052969, filed on Sep. 23, 2016, which claims the benefit of GB Patent Application No. 1516866.9, filed on Sep. 23, 2015. These applications are hereby incorporated by reference herein.

FIELD OF INVENTION

The present invention relates to cytological and histological analysis of tissue samples, and more particularly to methods of analysis of microscope images, for example of stained tissue samples, and apparatus therefor. Still more particularly the disclosure relates to the digital image processing of microscope images, for example slide scans, for the purposes of digital pathology.

BACKGROUND

Digital Pathology, which can also be referred to as virtual microscopy or virtual pathology involves managing, analysing and interpreting digital information. In this field of technology the need to make inter-image comparisons and to train learning algorithms on large volumes of data represents a significant challenge. Whole slide microscope images may comprise large volumes of data. The applicants have recognised a need to automate upload and processing of such data without compromising the ability of such methods to provide objective comparisons between different tissue samples acquired using different systems, Processes described herein may involve the generation of glass slides and converting these to digital pathology slides using digital pathology solutions. A digital slide scan is then generated which allows for high resolution viewing, interpretation and image analysis of digital pathology images. Growth in digital pathology solutions has totally transformed how research labs manage and interpret glass slides, with analysis and interpretation of histological images now conducted on a computer screen.

Gaining momentum globally, digital pathology is being used across health and pharmaceutical sectors, education and contract research organisations. With wide ranging applications the realised benefits of this sophisticated technology have encourage high growth in the market for digital pathology solutions, which by 2020 is estimated to be worth $5.7 billion.

The ability to provide accurate diagnosis is critical to the provision of healthcare. Biopsies to identify the presence of diseases such as cancer are a useful tool in such diagnosis. Accurate prognostic assessment is also critically important, because it enables action to be taken to counteract further development of disease. Microscope images of tissue samples have been used for these purposes for many years.

Large numbers of microscope imaging systems, each with their own particular characteristics, have been developed for this purpose. Whole slide imaging systems obtain digital images of entire microscope slides by scanning the field of view of a microscope across a macroscopic tissue sample to obtain a series of digital images. The resulting digital images can then be concatenated together to provide a single image, or image set, which describes the entire microscope slide. Partial images of slides can also be obtained by the same approach.

Pathologists involved in making diagnoses based on these kinds of images may rely on qualitative judgements. Such judgements may be based on their scientific knowledge and also on personal experience. This is necessarily a subjective process. As a result diagnoses, and prognostic assessments are not always reproducible—different pathologists may make different judgements based on identical images of tissue samples.

In making diagnostic judgements, the pathologist's task is made still more difficult because large tissue samples may be involved. In such cases many tens, or even hundreds of microscope images may need to be analysed from a single patient. This is particularly true where multiple tissue biopsies have been taken from a relatively large area of the body such as the prostate. These issues compound the problem of reproducibility because two different pathologists assessing the same patient's tissue sample may take into account features of different areas of different images of the same tissue sample.

The conditions under which a tissue sample was obtained, and the treatment of that sample before it was imaged (for example in terms of the concentration of stain applied to it), the imaging system used to acquire the image, and the presence of image artefacts may all cause variations between images. Although painstaking analysis is required, human pathologists are at least able intuitively to make allowances for such confounds. The subjective nature of assessment by human pathologists therefore, whilst problematic, at least provides one way to address these problems of inter-image variability. This need for intuitive judgement prevents straightforward automation of diagnostic and prognostic assessment of microscope images.

There are still further obstacles to overcome.

SUMMARY OF INVENTION

Aspects and examples of the invention are set out in the claims and aim to address technical problems such as those outlined above. Aspects and examples of the invention are also described herein.

BRIEF DESCRIPTION OF DRAWINGS

Embodiments of the disclosure will now be described, by way of example only with reference to the accompanying drawings, in which:

FIG. 1 includes a flow chart in FIG. 2A which illustrates an image processing method and data and vector diagrams in FIG. 2B illustrating colour data;

In the drawings like reference numerals are used to refer to like elements.

SPECIFIC DESCRIPTION

Figure 2:
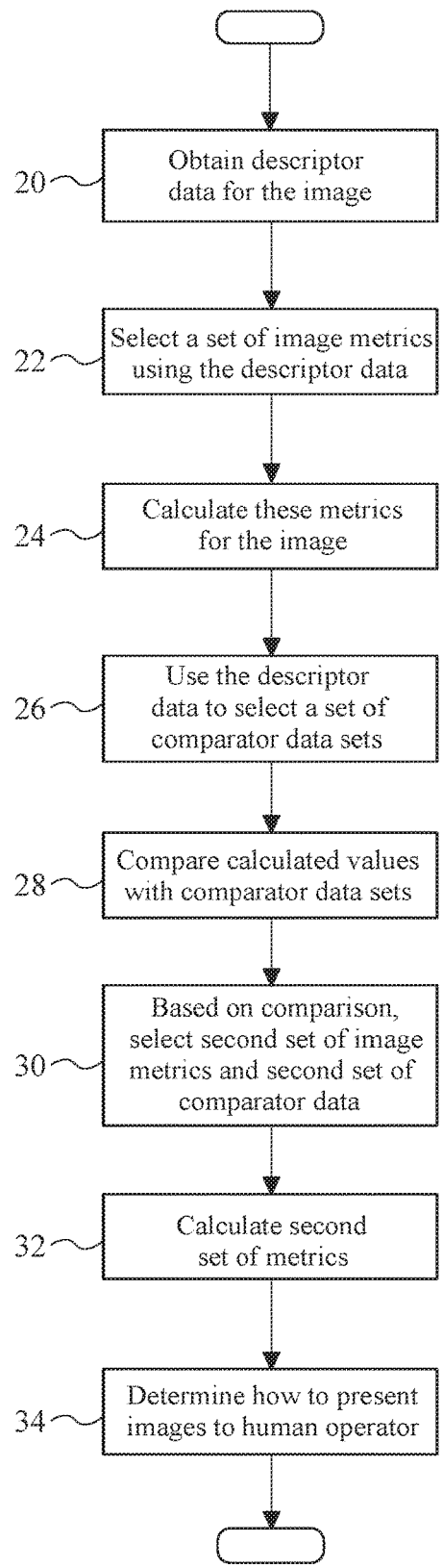
FIG. 2 illustrates a flow chart indicating a method of analysing image data.

FIG. 1 shows a pictorial representation of a process.

As illustrated in FIG. 1, embodiments of the disclosure relate to image processing methods and apparatus which aim to enable objective comparisons between images, and aim to improve the computational efficiency of automated diagnoses and prognostic assessments based on microscope images. This is done by normalising the image pixel data. To accomplish this, a computer obtains chunk colour data, the colour of each chunk representing a plurality of image pixels which make up that chunk. The computer also determines an approximate colour representation, one for each one those chunk colours. It will be appreciated in the context of the present disclosure that each chunk may comprise a contiguous spatial region of image data, such as a group of neighbouring pixels, for example a tile. For example the chunks (or tiles) together make up a low resolution version of the image—e.g. a lower magnification power version of the image.

As illustrated in FIG. 1, a method of the disclosure comprises obtaining a high power magnification image, for example by taking a slide scan or by retrieving image data of a slide scan from memory. The image is subsampled to provide data at lower image resolution, for example a 2× magnification or some other magnification level. Chunks of the subsampled image resolution data are selected, together these chunks may describe the entire image or just a region of interest in that image. A mapping transformation, such as a stain matrix and perhaps also stain concentration parameters, are then estimated based on this lower image resolution data for example using the methods explained below. The mapping transformation, for example the stain matrix, that is calculated from the subsampled, low resolution, data (for example the 2× magnification data) is then applied to higher resolution data—for example 5× magnification data, for example native resolution data. This process may be repeated for multiple regions of interest which together span all, or part, of the entire image for example all of the stained tissue regions in the image. The result is that normalised, high resolution, image data can be obtained.

The method illustrated in FIG. 1 uses these two sets of data to calculate a mapping transformation. This mapping transformation, determined from the image itself and the chunks which make it up, is then applied to each of the image pixels to obtain normalised image pixel data.

A chunk of image data comprises image data which represents a selected spatial region of the microscope image. The chunk may, for example, comprise a geometric or irregular shaped spatial region of an image, such as a tile. For example a chunk may be obtained by subsampling a high resolution (e.g. native resolution) version of a microscope image.

FIG. 1 illustrates one such computer implemented method. In this method, the computer first obtains 2 microscope image data for analysis. This microscope image data may comprise whole slide images. The image data often defines a microscope slide image of a haematoxylin and eosin stained tissue sample, but the slides may also be stained using saffron (as in HES staining). The data itself may be obtained from data storage in the computer's memory and/or may be received over a network. This data may also be obtained from a tissue sample by a microscope imaging system as part of the method and communicated directly to the computer. The image data may originate from a whole slide imaging system.

The computer then identifies 4, from the image data, image chunk data defining a plurality of image chunks. Each item of chunk data represents an area of the image which encompasses a plurality of image pixels. For example each item of chunk data may represent a single colour, for example using three colour component data elements of an additive mixing colour system. Those three colour component data elements can represent the colour of a chunk as a whole. Examples of three colour components include red, green, and blue—RGB data. RGB data may be represented in HSL or HSV format, or using any other format. Each item of chunk data may relate to a particular spatial region of the image. Each chunk may comprise groups of underlying pixels, and/or may be calculated from the pixels in the area of the image to which the chunk relates, or they may already exist as part of the image data. For example the image data may comprise a multi-resolution image format such as a pyramid TIFF. The computer stores image chunk data representing the colour of each chunk into a first memory location in a data storage memory of the computer.

The computer then determines 6, from this chunk data, two main contributions to the variance in the colours of those chunks. As noted above, the chunk colour data represents the colour of each chunk using an additive mixing of colour components, such as RGB data elements, which when mixed together represent the colour of that chunk as a whole. It will be appreciated in the context of the present disclosure that a set of chunk colours can be represented as a "point cloud" in a co-ordinate space defined by the colour components that are additively mixed to define the colour of each chunk (e.g. colour space). This distribution of the chunk data may be non-spherical—e.g. it may be elongated in one or more main "directions". These main "directions" in colour space are themselves, of course, also colours in the sense that they can be represented by an additive mixing of the colour components used to define the chunk data which makes up that distribution. To determine the main contributions to the variance, or spread, of the chunk data, the computer processes the chunk data to identify a set of colour contributions which include the colours of these main directions of the distribution of chunk data. The computer may achieve this by assembling the chunk colour data into a matrix in the computer memory. In this matrix, each column comprises the colour data elements of a corresponding single chunk. The computer processes this matrix using a decomposition method, such as principal component analysis, PCA, or singular value decomposition, SVD. The computer then selects the two vectors, $E_1$, $E_2$, or colour contributions, obtained from this decomposition which make the main contributions to the spread of the chunk colour data in colour space. For example it may select the vectors obtained from SVD which have the two largest singular values, or the vectors obtained from PCA which have the two largest eigenvalues. These may be stored into memory as unit vectors, $E_1$, $E_2$ aligned in colour space in the direction of these two main contributions The computer then uses the "direction" of these two largest contributions to calculate 8 an approximate representation of the colour of each chunk $T_i$. To do this, the computer may read each item of chunk colour data, $T_i$, from the memory location in which it has been stored. The computer can then fit the two main colour contributions to each item of chunk data to determine the additive combination of those two main contributions which best represents that item of chunk data. For example, the computer may multiply each colour data element of each item of chunk data by a corresponding colour data element of a corresponding one of the main contributions. By summing the results of these multiplications, the computer determines the scalar product of that item of chunk data and a unit vector in the direction of that main contribution. This provides a projection of each item of chunk data onto each of these two main contributions.

The computer then determines an angle, $\theta_i$, for each item of chunk data by calculating, from these scalar products, the arctangent of the ratio of (a) the scalar product of each item of chunk data, $T_i$, with a unit vector in the direction of the first of the two main contributions $E_1$ to (b) the scalar product of each item of chunk data, $T_i$, with a unit vector in the direction of the second of the two main contributions $E_2$. The computer then stores this angle, or a representation of it (for example its tangent) into memory. It will be appreciated however that, although the use of an angle approximation such as this is particularly useful, other ways of making (and recording) this same approximation may also be used. For example, the additive mixing of the two main contributions $E_1$, $E_2$ may be stored into memory for each item of chunk data, or the ratio of the amounts of those two contributions may be stored. The calculation of a scalar product is a computationally efficient way to determine this approximation, and a memory efficient way to record the combination of the two largest contributions that approximates each image chunk, but other approaches may also be used.

At this stage in the method two sets of data exist in the computer's memory. On the one hand, there is the chunk data, and on the other hand, for each item of that chunk data, a corresponding approximate representation of the colour of that chunk obtained from the two main contributions to the variance as explained above (e.g. in the form of an angle, $\theta_i$, for each chunk). In the next stage of the method, the computer uses the approximate representations, and the image chunks to calculate 10 a mapping transformation. This mapping transformation, which may be referred to as a stain matrix. This mapping transformation is configured to transform each item of the chunk data on to a corresponding normalised representation of that chunk.

To calculate the mapping transformation the computer identifies the approximate representation, vMin, which is most similar to a first one, $E_1$, of the two main contributions $E_1$, $E_2$. Where the approximations are stored as angles $\theta_i$, this may be done by identifying the smallest (e.g. the minimum) of those angles $\theta_{min}$. The computer also identifies the approximate representation, vMax, which is most similar to the second one of those two main contributions $E_1$, $E_2$. Where the approximations are stored as angles $\theta_i$, this may be done by the computer identifying the largest (e.g. the maximum) of those angles $\theta_{max}$. Where the approximations are stored as angles $\theta_i$ the computer may calculate (reconstruct) the approximate representations, vMin, vMax from the angle data by performing the following trigonometric scaling:

$$v\text{Min} = E_1 \cos(\theta_{min}) + E_2 \sin(\theta_{min})$$

$$v\text{Max} = E_1 \cos(\theta_{max}) + E_2 \sin(\theta_{max})$$

A physical interpretation of these two unit vectors is that they are the intensity normalised items of chunk data which most closely resemble each of the two main contributions to the variance in the colours of the chunk data. It will be appreciated that, instead of using this trigonometric scaling, a unit vector could be determined from each of the items of chunk data which correspond to $\theta_{min}$ and $\theta_{max}$ respectively. However, the use of a trigonometric scaling may provide computational efficiency gain. The computer may then use these two unit vectors, vMin, vMax to provide the mapping transformation. For example, the mapping transformation may comprise a matrix (or an array of computer memory locations) storing these two unit vectors together.

The computer then stores this mapping transformation in a fourth computer memory location, and iterates through the items of image pixel data, applying 12 this mapping transformation to the three colour component data elements of the each image pixel to obtain normalised pixel data for each image pixel. The computer may apply the mapping transformation by determining an additive mixture of the two vectors vMin and vMax which approximates the colour of each image pixel. For example this may be done by the computer projecting each item of pixel data separately onto the vectors vMin and vMax which are stored in the mapping transformation (stain matrix). For example, the scalar product of each item of pixel data with vMin may provide one colour channel value (e.g. the haematoxylin channel) for that item of pixel data, and the scalar product of each item of pixel data with vMax may provide the other colour channel value (e.g. the eosin channel). The computer may also determine the stain concentration by determining the inverse of the stain matrix, and multiplying the inverse of the mapping transformation (stain matrix) by the colour vector for each image pixel. It will be appreciated that the colour vector for each image pixel may comprise the optical density of that image pixel (this is explained below with reference to FIG. 2).

The computer may then assemble the resulting normalised pixel data to provide a complete, normalised, image. This normalised image may then be provided, for example by being stored into a computer readable data storage and/or by being transmitted over a network to enable further analysis. This normalisation may assist in the provision of objective measures of image features.

FIG. 2 shows a flow chart illustrating a computer implemented data analysis method. In the method illustrated in FIG. 2, the computer comprises a processor and a computer memory as described above with reference to FIG. 1. In addition, the memory of the computer used to implement the method of FIG. 2 stores an association between a plurality of items of descriptor data, for example in the form of labels and, for each item of descriptor data at least one corresponding set of comparator data for each descriptor. Each set of comparator data comprises comparator data values indicating the values of quantitative image metrics obtained from the type of tissue identified by the corresponding descriptor. The descriptor data may include descriptors for breast tissue, prostate tissue, lung tissue, pancreatic tissue and other types of tissue. Each of these comparator data sets is in turn associated with a different tissue structure known to exist in the tissue type. For example, the descriptor for breast tissue may be associated in the computer memory with a comparator data sets for each of: fat tissue, blood vessels, ducts, lobules, LCIS (lobular carcinoma in situ), DCIS (ductal carcinoma in situ), and one or more types of tumour. Each of these comparator sets comprises data values for a set of quantitative image metrics such as optical density, texture data, spatial frequency data, cell size and shape, and morphological characteristics for the corresponding comparator tissue structure.

With this data accessible in memory, the method illustrated in FIG. 2 proceeds as follows. Firstly, the computer obtains 20 descriptor data, perhaps provided with the microscope image data that indicates a type of tissue from which the tissue sample originates. Then, the descriptor data is used to select 22, from data storage in the computer memory a set of quantitative image metrics.

The computer then calculates 24 this first set of quantitative metrics from sample image data (which may comprise normalised image data such as that obtained using a method according to that illustrated in FIG. 1). By calculating these metrics, the computer obtains a data value for each of this first set of quantitative image metrics for the sample image data. These data values can then be stored in the computer memory, which may also store an association between the particular data values and the sample image.

The computer then uses 26 the descriptor data to obtain a set (or sets of) comparator data values (e.g. values of these quantitative image metrics) from the computer memory. For example the computer memory may comprise a look-up table or other memory reference structure which permits the comparator data values to be selected using the descriptor data as an index.

The computer then compares 28 the data values obtained from the sample image at least one of these comparator sets of data values. The computer then iteratively steps through the groups of data (e.g. regions of the image and/or chunks) which make up the sample image, and compares the data values for the set of quantitative metrics for these groups with the comparator data.

Based on these comparisons some parts of the sample image data may be identified as belonging to one or more of the tissue structures described by the comparator data sets. One or more of these comparator data sets may correspond to tissue types which are known to look similar to certain types of cancer, or to be pre-cancerous. Examples of such tissue structures include LCIS and DCIS in breast tissue, but other such examples exist. In the event that the computer identifies one of these selected types of tissue, it can partition the image data into at least two subsets. Each of these subsets may correspond to one of these types of tissue structure, or to a certain class of tissue structure.

The computer then subjects each of the two subsets of data to different analysis. The computer selects 30 a subsequent analysis step for each subset of the data based on both (a) the type of tissue as identified by the descriptor data and (b) the tissue structure identified by the comparator data set that matched each subset. For example, the computer may exclude one or more of the subsets from subsequent analysis. As another example the computer may select a second set of quantitative image metrics to be applied 32 to one of the subsets of data by using the identity of the comparator tissue structure that matched that subset. This second set of quantitative metrics may comprise low level (e.g. high resolution) image metrics, which may comprise metrics which describe the size and shape of cell nuclei.

The computer can apply the method described above to a plurality of images, and to a number of individual regions of those images. In these embodiments the computer stores, in memory, an association between each of images and/or each of those regions and a score that is based on (a) the descriptor data indicating the tissue type from which the tissue sample originated (b) the match between those images or regions and the comparator data sets (for example the statistical confidence level of such a match). The computer then selects 34 a sequence in which to present the slide images to a human operator based on that score. The computer may also highlight particular regions of the images based on the score associated with those image regions.

Figure 3:
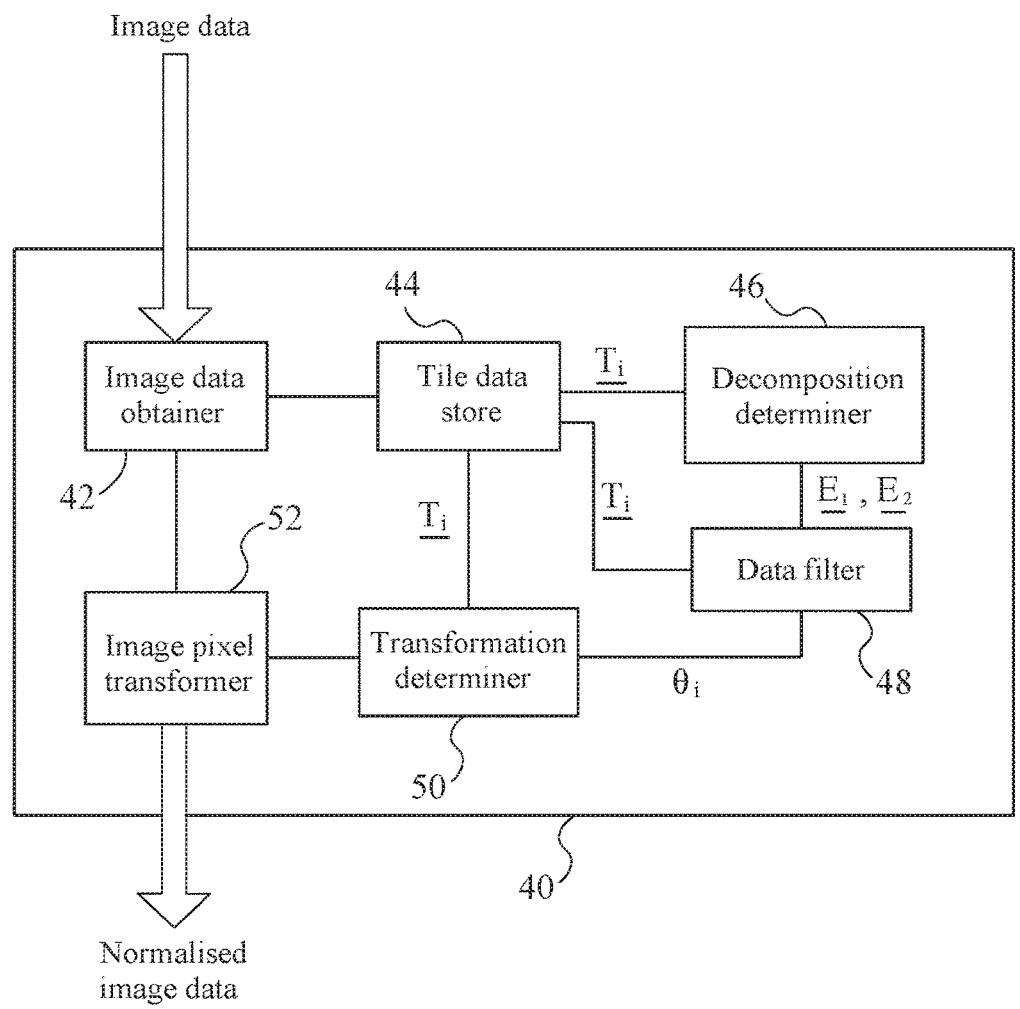
FIG. 3 shows a very schematic illustration of an image processing apparatus.

FIG. 3 illustrates an image processing apparatus 40 configured to perform an example of a method according to FIG. 1.

The apparatus 40 of FIG. 3 comprises an image data obtainer 42, a chunk data store 44, a decomposition determiner 46, a data fitter 48, a transformation determiner 50, and an image pixel transformer 52. Although not shown in the drawings, each of these elements generally comprises computer readable storage, and logic modules, which may be realised in hardware such as combinations of logic gates and/or programmable logic such as field programmable gate arrays, FPGA, and/or application specific integrated circuits, and or by general purpose programmable processors in combination with appropriately configured firmware and software. One or more of these elements may be configured to provide efficient processing of vector data and/or matrices. Accordingly, the embodiment of FIG. 3 will be described with reference to vector operations, but it will be appreciated that such operations may also be implemented as iterative, step wise, operations applied sequentially to each of a series of data values.

Each of the elements of the apparatus 40 shown in FIG. 3 is coupled to communicate data and/or commands to one or more of the others. In particular, the image data obtainer 42 is coupled to the chunk data store 44 and to the image pixel transformer 52. The decomposition determiner 46 is coupled to the chunk data store 44, and to the data fitter 48. The transformation determiner 50 is coupled to the chunk data store 44, the data fitter 48, and to the image pixel transformer 52.

The data obtainer 42 comprises a data communication interface for obtaining microscope image data defining microscope slide images of haematoxylin and eosin stained tissue samples. Examples of data communication interfaces include Ethernet, and serial interfaces such as a universal serial bus interface—other examples of data communication interface maybe used.

The chunk data store 44 comprises data storage memory for storing chunk data comprising three colour component data elements representing the overall colour of the each image chunk. This and other computer memory described herein may comprise volatile and/or non-volatile memory—for example random access memory, RAM, or on-chip cache memory, hard disc drives, HDD, or solid state drive, SSD.

The decomposition determiner 46 is adapted to obtain the chunk data from the chunk data store 44, and to calculate the two main contributions to the variations of that chunk colour data as explained above with reference to FIG. 1. The decomposition determiner 46 of FIG. 3 is adapted to apply singular value decomposition to vector data to obtain a set of basis vectors which describe the variance in that data.

The image pixel transformer 52 comprises an output interface (e.g. a data communication interface as described above) adapted to provide output image data for example to store that data into a computer readable data storage and/or to transmit it over a network to enable further analysis.

In operation, the data obtainer 42 obtains a digital image of a microscope slide carrying a haematoxylin and eosin stained tissue sample. The data obtainer 42 stores chunk data from this image into the chunk data store 44. This data comprises a colour vector for each chunk in the form of three colour components representing the colour of that chunk.

The decomposition determiner 46 then assembles these colour vectors into a matrix in which each column of the matrix is provided by one of the chunk colour vectors. The decomposition determiner 46 calculates a singular value decomposition of this matrix. The results of this SVD process include (a) a plurality of basis vectors and selected so that each of the plurality of colour vectors can be represented as a linear combination of those basis vectors, and (b) a corresponding set of values which define the contribution of each basis vector to the total variance of the chunk data. The decomposition determiner selects the basis vectors which correspond to the two largest values in this singular value decomposition and provides these two bass vectors (each of which comprises three colour component data elements) to the data fitter.

The data fitter 48 then retrieves, from the chunk data store 44, each of the chunk vectors and determines the projection of each chunk vector onto the two basis vectors provided by the decomposition determiner. This provides an approximate representation of each chunk in terms of the two basis vectors, and excluding colour contributions to the chunk data which are not aligned with those two basis vectors (e.g. colours associated with the other Eigenvectors from the SVD). This projection may be done by calculating the scalar product of each of the two basis vectors with each chunk colour data. The result of this operation is that each chunk vector is represented by an approximate two component representation, each of these two components being a contribution from one of these two basis vectors. The data fitter then determines the arctangent of these two components to derive an angle, θ, for each chunk. The data fitter 48 then provides these angle data values to the transformation determiner.

The transformation determiner 50 takes these θ data values, retrieves the chunk data from the chunk data store 44, and determines a mapping transformation matrix. This mapping transformation may be referred to as a stain matrix. The image pixel transformer 52 then retrieves each of the image pixels which makes up the image from the image data obtainer and applies the mapping transformation to transform each image pixel of the image data.

To calculate the mapping transformation the transformation determiner identifies the minimum of the θ data values, $\theta_{min}$, and the maximum of the θ data values, $\theta_{max}$. The transformation determiner then determines two unit vectors, vMin, vMax from the angle data by performing the following trigonometric scaling:

$$v\text{Min} = E_1 \cos(\theta_{min}) + E_2 \sin(\theta_{min})$$

$$v\text{Max} = E_1 \cos(\theta_{max}) + E_2 \sin(\theta_{max})$$

where $E_1$ and $E_2$ each comprise a set of data elements which describe the additive mixture of colours (whether in RGB or optical density space) which account for the two largest components of the variance in the colour data. These sets of data values, $E_1$ and $E_2$ may be described as vectors, but it will be appreciated that these are real physical quantities describing a real world parameter—namely the colours of (or at least an approximation to the colours of) the haematoxylin and eosin stains in the image.

A physical interpretation of the two unit vectors, vMin, vMax is that these two sets of data values (each representing the additive mixture of colours of a particular chunk from the microscope image data), is that they are intensity normalised versions of the particular items of chunk data which most closely resemble each of the two main contributions to the variance in the colours of the chunk data. For example they are the unit colour vectors representing the appearance of each of the two stains in the chunks of image data. As noted above, instead of using this trigonometric scaling, a unit vector could be determined from each of the items of chunk data which correspond to $\theta_{min}$ and $\theta_{max}$ respectively. However, the use of a trigonometric scaling may provide computational efficiency gain. The transformation determiner may then use these two unit vectors, vMin, vMax to provide the mapping transformation. For example, the mapping transformation may comprise a matrix (or an array of computer memory locations) storing these two unit vectors together.

The apparatus of FIG. 3 may therefore be configured to perform a computer implemented image processing method such as that described above with reference to FIG. 3. Other configurations of hardware may also be used to perform the same method, and methods similar to it. It will be appreciated that the underlying image data is fundamentally transformed from a non-normalised state, into a normalised state by the application of the mapping transformation. For example, by calculating the projection of the image pixels onto each of the vectors vMin, vMax, the image pixel data (whether that be optical density or RGB data) is transformed into two colour channels.

The hardware elements described with reference to FIG. 3 may each be implemented with fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic. They may also be implemented using a general purpose processor programmed with a combination of firmware and software, code. The data storing elements may comprise volatile or non-volatile memory such as flash memory, optical disks, CD-ROMs, DVD ROMs, magnetic or optical cards, other types of machine-readable mediums suitable for storing electronic instructions, or any suitable combination thereof.

One example of a method according to FIG. 1 comprises obtaining microscope image data defining a microscope slide image of a haematoxylin and eosin stained tissue sample. The microscope slide image comprises a plurality of image chunks spanning the image of the tissue sample. Each chunk comprises image pixel data representing a plurality of image pixels. This method also comprises obtaining colour vector data defining a plurality of colour vectors from this image data. Each colour vector is based on the colour of a corresponding one of the plurality of image chunks, and each comprises at least three colour components representing a colour of haematoxylin and eosin stained tissue sample in the corresponding image chunk. In this method the colour vectors are then used to determine a plurality of basis vectors, for example using PCA or SVD, selected so that each of the plurality of colour vectors can be represented as a linear combination of those basis vectors. For example, the basis vectors may form an orthogonal or orthonormal set. The method also comprises selecting, from this plurality of basis vectors, the two basis vectors which together account for most of the variance in the chunk colour vectors. These two basis vectors are then used to determine a unit vector consisting of a contribution from each of the two basis vectors—for example by projecting each chunk vector onto the two basis vectors. This unit vector may be expressed as an angle, θ, for each image chunk. The next step in the method is to determine a transformation, for example in the form of a matrix that transforms each chunk colour vector on to its corresponding unit vector. This matrix, determined from the chunk data, may be referred to as a stain matrix. The stain matrix is then applied to the image pixels to obtain normalised image pixel data.

The apparatus of FIG. 3 may also comprise a data store, and a computer processor configured to perform the data comparison, analysis, and sequencing/highlighting steps described above with reference to FIG. 2.

Figure 4:
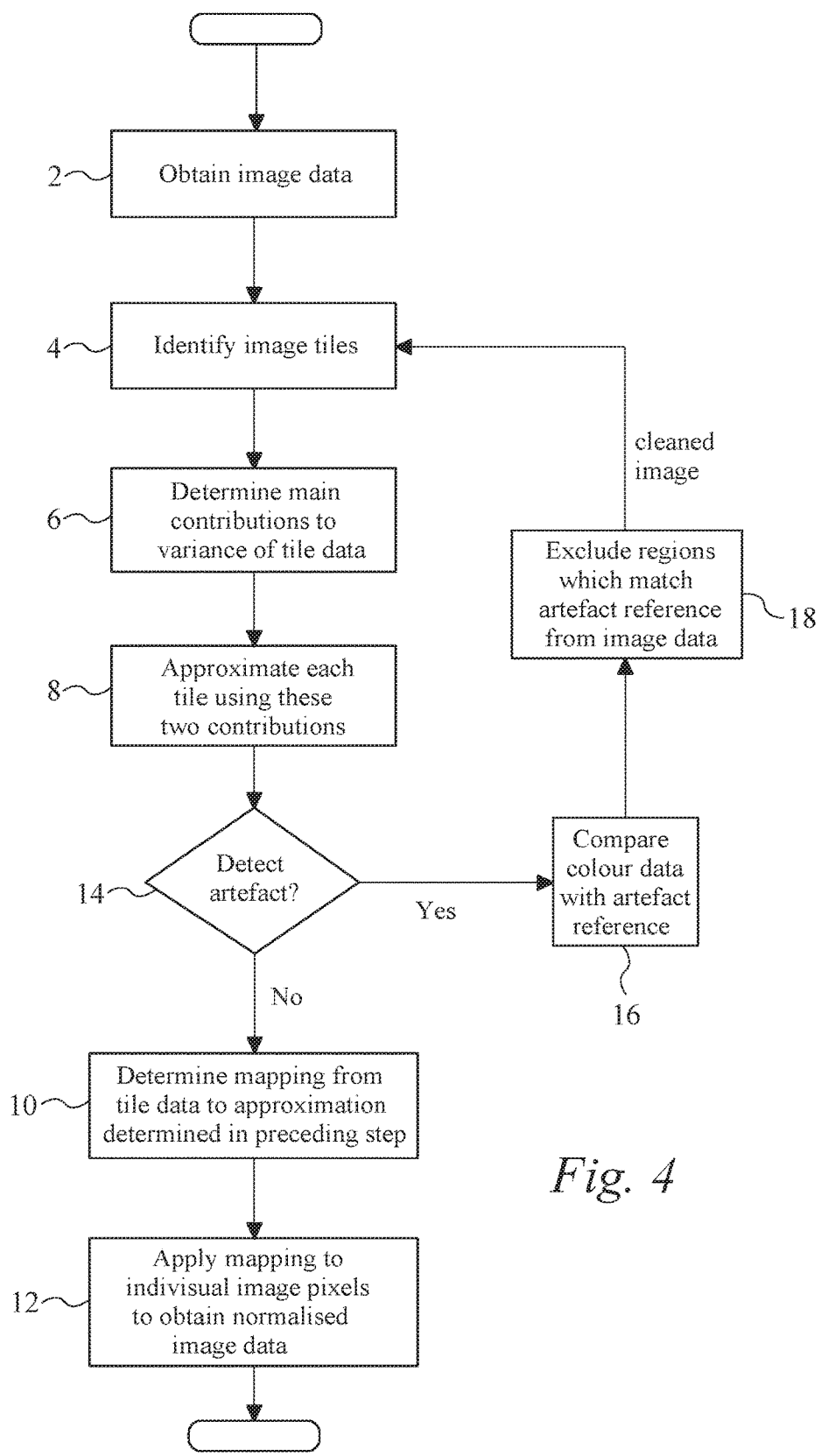
FIG. 4 shows a further example of the method illustrated in FIG. 1.
Figure 5:
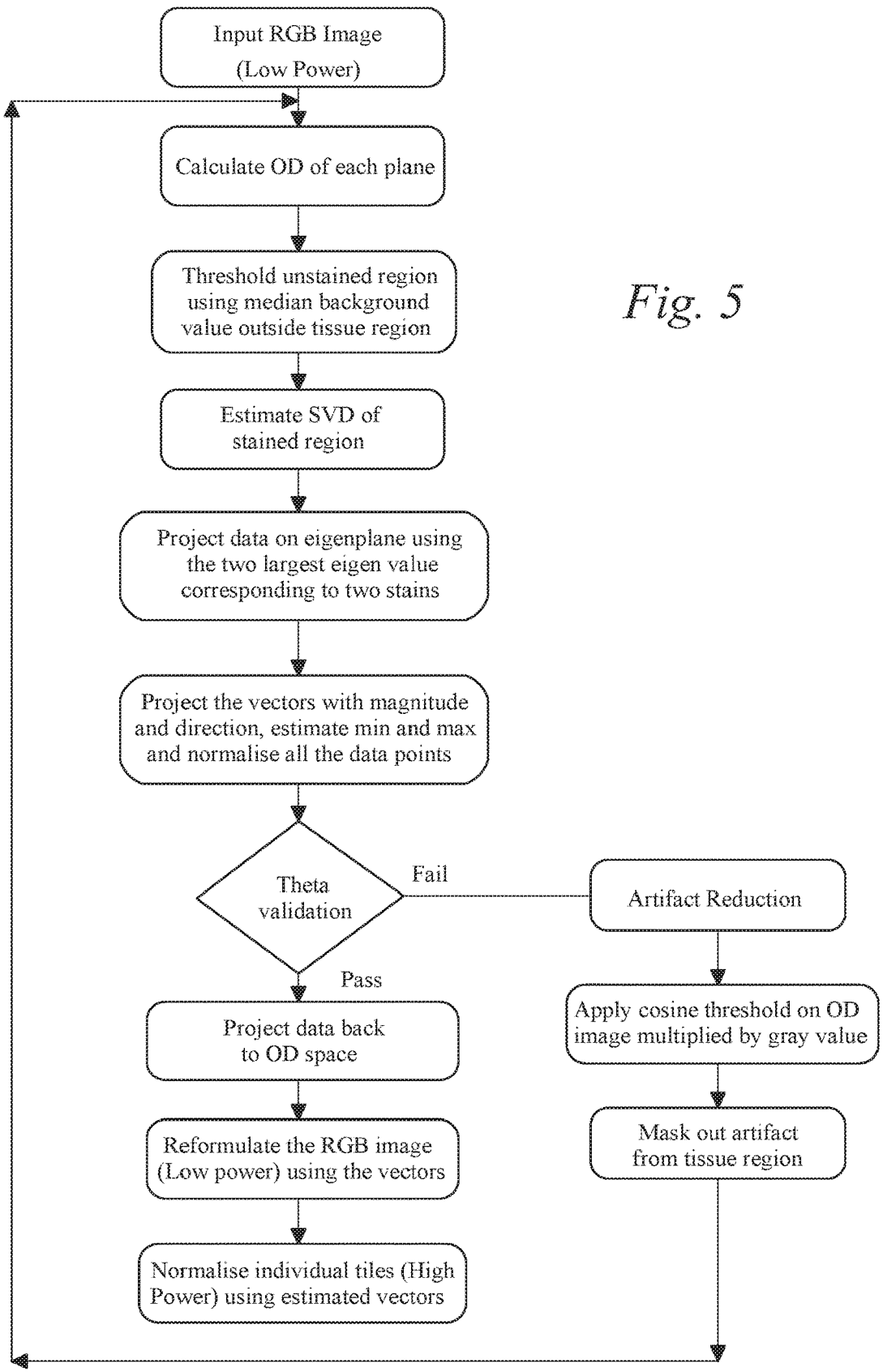
FIG. 5 shows a further example of the method illustrated by FIG. 1.

FIG. 4 illustrates a computer implemented method which may be of particular utility in the automated processing of large numbers of microscope images. These methods may be particularly useful where the quality of such images is unknown.

It will be seen that FIG. 4 illustrates a method which has a number of features in common with FIG. 1. In particular, the method of FIG. 4 includes, with reference to FIG. 1, the obtaining step 2, the identification of image chunk data 4, the determination of the two main contributions to the variance in the colours of those chunks 6, and the use 8 of these two largest contributions to calculate an approximate representation of the colour of each chunk in the form of a unit vector or "direction" (e.g. the angle, θ).

The method illustrated in FIG. 4 however also comprises some additional steps which permit the computer to identify and reject certain image confounds and artefacts. This may enable high throughput, automated, processing of microscope images.

In the method of FIG. 4, to detect 14 the presence of artefact in an image, the computer compares the approximate representations of the image chunks with an allowed range. The computer then determines whether the values of these approximations, for example the values of the angle θ, lie outside a selected range. This may be determined by comparing the mean or median value with a first predetermined range, and/or by determining whether more than a selected number of image chunks lie outside a second predetermined range.

In the event that these criteria are met, this can indicate the presence of artefact in the microscope image. In response, the computer compares 16 at least one of the image pixel data and the chunk colour data with known artefact colour reference data to identify regions of that microscope image which match the artefact colour. Examples of artefact colour reference data include data in which the RGB values are all equal, for example greyscale data. Other examples of artefact colour reference data may be used.

The computer may test for this match by calculating the scalar product of the artefact colour reference data and the image data (e.g. the chunk data and/or the image pixel data as the case may be). The computer may also scale the result of this scalar product by the magnitude of the image data to normalise it before comparing the result with a match threshold. In the event that the scalar product of the artefact data and the image data exceeds this match threshold, the computer excludes 18 the relevant image data (chunks and/or regions of pixels) from the microscope image data, to obtain cleaned image data.

The computer then recalculates 6 the two largest components, and the approximated image chunks 8 based on the cleaned image data before the calculating of the mapping transformation 10 and the normalised image pixel data 12 as explained above with reference to FIG. 1.

It will be appreciated in the context of the present disclosure that the chunk colour data may comprise optical density data, and the computer may be configured to process chunk data obtained from the microscope images by first determining the optical density of each chunk. This may be determined based on a logarithm, for example a natural logarithm, of the colour component data elements of each chunk in the microscope image data. In addition, prior to determining the two main contributions to the variance of the chunk data as described above, the computer may exclude from the analysis chunks relating to background regions of the image (e.g. regions with no tissue, or no stained tissue in them) by applying a threshold to the chunk data. Sub-threshold chunks, or parts of chunks, may be excluded from the analysis—for example the computer may exclude subthreshold chunks, or parts of chunks, from the data which is used to determine the main contributions to the variance. The computer may apply the threshold to the logarithmic, optical density, chunk data for this purpose. The threshold may comprise a threshold in one or more colours, or it may comprise an intensity threshold (e.g. based on the sums of squares of the colour data elements). This threshold may be selected empirically, e.g. the method may comprise prompting a human operator to provide a threshold, for example by selecting a background region of one or more images. In some embodiments, the threshold is selected by the computer, for example it may be predetermined.

It will also be appreciated in the context of the present disclosure that this image data may originate from any one of a plurality of different classes of imaging system. These systems may each use different image acquisition protocols, and different types of optics. For example, some systems acquire a series of monochrome images each using a different one of a series of different colour filters. The resulting monochrome images can then be combined to provide a colour image of a sample in discrete, well defined, colour bands. Other systems use colour cameras in combination with multi-band filters. Such filters may have for example three predefined colour pass-bands so as to generate colour images in a single shot. The pass bands may be selected based on the characteristics of the sample or analysis technique. Some examples of whole slide imaging systems include the Aperio ScanScope FL (available from Aperio, Vista, Calif.), the Leica SCN400F (available from Leica Biosystems, Richmond, Ill.), and the 3DHistech P250 (available from 3DHistech, Budapest, Hungary) is an example of this kind of scanner. Other examples of whole slide imaging systems exist and no doubt will be developed in future—embodiments of the disclosure may permit the processing of, and comparison between, image data originating from any one or more of such systems.

The embodiments described above make reference to the use of Pyramid TIFF images as one example of a multi-resolution image format. Other types of image format may of course be used. It will also be appreciated that TIFF is a tag-based file format for storing and interchanging raster images. A TIFF file can hold multiple images in a single file. A Pyramid TIFF may comprise a TIFF file that includes a sequence of bitmaps that each represent the same image at increasingly coarse spatial resolutions. The individual images may be compressed or tiled. Compression is used when storage space savings are significant; tiling may yield more efficient delivery when most use involves zooming into image sections rather than viewing the whole. The term Pyramid TIFF or pyramid-encoded TIFF has been applied to different approaches, each based on valid internal TIFF structures, that have been used to support dynamic delivery of the underlying image at different spatial resolutions. Pyramid TIFF files created by different applications are not necessarily the same in structure. It is to be understood that the specific details of this, or any other, image format, whilst useful in some instances are not an essential feature of the present disclosure.

Whole slide microscope images may have a resolution of a few hundred nanometers, for example 250 nm. The tissue samples themselves may each be ten millimeters across or more, for example about 15 mm by 15 mm. Whole slide images of such samples may comprise at least $10^8$ pixels, for example at least $10^9$. In some embodiments whole slide images comprise $10^8$ to $10^{10}$ pixels.

To the extent that certain methods may be applied to the living human or animal body, it will be appreciated that such methods may not provide any surgical or therapeutic effect. In addition, it will be appreciated that such methods may be applied ex vivo, to tissue samples that are not part of the living human or animal body. For example, the methods described herein may be practiced on meat, tissue samples, cadavers, and other non-living objects.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

It will be appreciated that, although the mapping transformation is described as being calculated by determining the unit vectors vMin, vMax, of the measured chunk data which correspond most closely to the largest contributions to the variance in the colour data (e.g. the Eigenvectors which correspond to the largest Eigenvalues, or the principal components of the variance), the transformation may be calculated in other ways. For example it may be calculated numerically, for example by determining a merit function which relates the characteristics of the transform to a measure of the sum of residuals between each item of chunk data and the corresponding approximate representation of that item of chunk data. For example it may be determined by a linear or non-linear numerical optimisation. Suitable methods for numerical optimisation can be selected by the skilled addressee in the context of the present disclosure. Examples are described in *Numerical Recipes 3rd Edition: The Art of Scientific Computing: Published by Cambridge University Press*. Any other appropriate way of calculating the mapping transformation may also be used. The mapping transformation may be selected to map each of the chunk colours on to its corresponding approximate representation.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The activities and apparatus outlined herein may be implemented with fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

The invention claimed is:

1. A computer implemented image processing method comprising:
    obtaining microscope image data defining a microscope slide image of a haematoxylin and eosin stained tissue sample, wherein the microscope slide image data comprises a plurality of image chunks and each chunk comprises image pixel data representing a plurality of image pixels;
    storing, in a first computer memory location, chunk colour data comprising, for each image chunk, three colour component data elements representing a colour of the each image chunk in three colour components;
    calculating, from the chunk colour data, two largest contributions to the variations of the chunk colour data wherein each of the largest contributions comprise three colour component data elements representing the each contribution in said three colour components, and storing the two largest contributions in a second computer memory location;
    calculating, for each image chunk, a combination of the two largest contributions that approximates a representation of the three colour component data elements of the each image chunk, thereby to provide a plurality of approximated image chunks, and storing the approximated image chunks in a third computer memory location;
    determining, from the approximated image chunks:
        (i) a first item of approximated image chunk data, vMin, that corresponds to a first one of the two largest contributions, and
        (ii) a second item of the approximated image chunk data, vMax, that corresponds to a second one of the two largest contributions,
    wherein the first item of approximated image chunk data and the second item of approximated image chunk data together provide a mapping transformation; and
    storing the mapping transformation in a fourth computer memory location;
    for each image pixel, obtaining image pixel data comprising three colour component data elements of the each image pixel, and transforming the colour component data elements of the each image pixel using the mapping transformation to calculate normalised image pixel data for the each image pixel;
    obtaining, from the third computer memory location, the approximated image chunks, and comparing the approximated image chunks with an allowed colour range to identify the presence of artefact in the microscope image; and wherein, in the event that an artefact is identified, at least one of the image pixel data and the chunk colour data is compared with artefact colour reference data to identify an artefact region of the microscope image that matches the artefact colour reference data.

2. The method of claim 1 comprising providing a normalised image comprising the normalised image pixel data.

3. The method of claim 1 comprising excluding chunk colour data having an optical density value that is less than a selected threshold from the calculation of the two largest components and from the calculation of the mapping configuration.

4. The method of claim 1 comprising obtaining, from the second memory location, the two largest contributions, and determining whether the colour data elements of the two largest contributions lie within a selected set of ranges to identify the presence of artefact in the microscope image.

5. The method of claim 1 comprising excluding the artefact region from the microscope image data, and at least one of the image pixel data and the chunk colour data to obtain cleaned image data.

6. The method of claim 5 comprising recalculating the two largest components, and the approximated image chunks based on the cleaned image data before the calculating of the mapping transformation and the normalised image pixel data.

7. The method of claim 6 wherein the representation of each approximated image chunks comprises two approximation data values, wherein each one of said approximation data values comprises a scaling of a corresponding one of said two largest contributions.

8. The method of claim 1 wherein calculating, from the chunk colour data, two largest contributions to the variations of the chunk colour data comprises determining an Eigen-decomposition of the chunk colour data.

9. The method of claim 1 wherein the image data is obtained by sampling a 2× magnification version of the original image to obtain parameters to apply to each chunk.

10. The method of claim 1 wherein the first item of approximated image chunk data, vMin comprises an intensity normalised item of the approximated chunk data which most closely matches the first one of the two largest contributions, and
wherein the second item of the approximated image chunk data, vMax, comprises an intensity normalised item of the approximated chunk data that most closely matches the second one of the two largest contributions.

11. The method of claim 10 wherein using the mapping transformation to calculate normalised image pixel data comprises projecting each item of image pixel data onto the first item of approximated image chunk data, vMin, to provide a first colour channel of the image pixel data.

12. The method of claim 11 wherein using the mapping transformation to calculate normalised image pixel data comprises projecting each item of image pixel data onto the second item of approximated image chunk data, vMax, to provide a second colour channel of the image pixel data.

13. The method of claim 12 wherein using the mapping transformation to calculate normalised image pixel data comprises determining stain concentration data.

14. A computer program product comprising program instructions operable to program a processor to perform the method of claim 1.

15. An image processing apparatus configured to perform the method of claim 1.

16. The computer program product of claim 14, further comprising program instructions operable to program a processor to perform providing a normalised image comprising the normalised image pixel data.

17. The image processing apparatus of claim 15 further configured to perform providing a normalised image comprising the normalised image pixel data.

18. The computer program product of claim 14, further comprising program instructions operable to program a processor to perform excluding chunk colour data having an optical density value that is less than a selected threshold from the calculation of the two largest components and from the calculation of the mapping configuration.

19. The image processing apparatus of claim 14, comprising excluding chunk colour data having an optical density value that is less than a selected threshold from the calculation of the two largest components and from the calculation of the mapping configuration.

20. The computer program product of claim 14, wherein using the mapping transformation to calculate normalised image pixel data comprises determining stain concentration data.

21. A computer program product comprising program instructions operable to program a processor to perform:
obtaining microscope image data defining a microscope slide image of a haematoxylin and eosin stained tissue sample, wherein the microscope slide image data comprises a plurality of image chunks, the chunkscomprising image pixel data representing a plurality of image pixels;
storing, in a first computer memory location, chunk colour data comprising, for each image chunk in the plurality, three colour component data elements representing a colour of the each image chunk in three colour components;
calculating two largest contributions to the variations of the chunk colour data wherein each of the largest contributions comprise three colour component data elements representing the each contribution in said three colour components, and storing the two largest contributions in a second computer memory location;
calculating, for each image chunk in the plurality, a combination of the two largest contributions that approximates a representation of the three colour component data elements of the each image chunk, thereby to provide a plurality of approximated image chunks, and storing the approximated image chunks in a third computer memory location; providing a mapping transformation; and
storing the mapping transformation in a fourth computer memory location;
for each image pixel in the plurality, obtaining image pixel data comprising three colour component data elements of the each image pixel, and transforming the colour component data elements of the each image pixel using the mapping transformation to calculate normalised image pixel data for the each image pixel;
obtainingthe approximated image chunks, and comparing the approximated image chunks with an allowed colour range to identify the presence of artefact in the microscope image; and wherein, in the event that an artefact is identified, at least one of the image pixel data and the chunk colour data is compared with artefact colour reference data to identify an artefact region of the microscope image that matches the artefact colour reference data.

* * * * *